US006290853B1

(12) United States Patent
Allmer et al.

(10) Patent No.: US 6,290,853 B1
(45) Date of Patent: Sep. 18, 2001

(54) CHROMOTOGRAPHIC METHOD AND DEVICE IN WHICH A CONTINUOUS MACROPOROUS ORGANIC MATRIX IS USED

(75) Inventors: Klas Allmer, Täby; Eva Berggren, Uppsala; Eva Eriksson, Stockholm; Anders Larsson, Bromma; Ingrid Porrvik, Uppsala, all of (SE)

(73) Assignee: Amersham Pharmacia Biotech AB, Uppsala (SE)

( * ) Notice: Subject to any disclaimer, the term of this patent is extended or adjusted under 35 U.S.C. 154(b) by 0 days.

(21) Appl. No.: 09/068,754
(22) PCT Filed: Nov. 20, 1996
(86) PCT No.: PCT/SE96/01508
  § 371 Date: Feb. 22, 1999
  § 102(e) Date: Feb. 22, 1999
(87) PCT Pub. No.: WO97/19347
  PCT Pub. Date: May 29, 1997

(30) Foreign Application Priority Data

Nov. 24, 1995 (SE) .................................................. 9504205

(51) Int. Cl.$^7$ .................................................. B01D 15/08
(52) U.S. Cl. ...................... 210/635; 210/656; 210/198.2; 210/502.1
(58) Field of Search .................................. 210/635, 656, 210/198.2, 502.1; 422/70; 436/161; 95/88; 96/101

(56) References Cited

U.S. PATENT DOCUMENTS

| | | | |
|---|---|---|---|
| 4,522,953 | * 6/1985 | Barby | 521/64 |
| 4,965,289 | * 10/1990 | Sherrington | 521/53 |
| 5,066,784 | * 11/1991 | Sherrington | 530/334 |
| 5,334,310 | * 8/1994 | Frechet | 210/198.2 |
| 5,453,185 | * 9/1995 | Frechet | 210/198.2 |
| 5,723,601 | * 3/1998 | Larsson | 536/165 |
| 5,728,457 | * 3/1998 | Frechet | 210/635 |
| 5,833,861 | * 11/1998 | Afeyan | 210/656 |
| 5,935,429 | * 8/1999 | Liao | 210/198.2 |

FOREIGN PATENT DOCUMENTS

| | | | |
|---|---|---|---|
| WO 90/07965 | * 7/1990 | (WO) | 210/198.2 |
| WO 95/31485 | * 11/1995 | (WO) | 210/198.2 |

* cited by examiner

Primary Examiner—Ernest G. Therkorn
(74) Attorney, Agent, or Firm—Royal N. Ronning, Jr.

(57) ABSTRACT

A chromatographic method and device for separating one or several organic substances in a liquid sample. According to the method said sample of substances is passed through a chromatographic device containing as separation medium at least one continuous macroporous matrix. The macroporous matrix comprises a cross-linked organic polymer prepared by polymerization of a high internal phase emulsion system of a water-in-oil emulsion of organic monomers, said emulsion containing at least 75% by weight of water phase. The polymerization results in an open porous structure, to allow a convective flow to pass through the macroporous matrix, whereby said organic substances separate from each other and/or the liquid. The pores of the macroporous matrix are unmodified, or surface modified in a manner that the convective flow is not hampered.

19 Claims, 4 Drawing Sheets

# CHROMOTOGRAPHIC METHOD AND DEVICE IN WHICH A CONTINUOUS MACROPOROUS ORGANIC MATRIX IS USED

REFERENCE TO RELATED APPLICATIONS

This application is a 371 of PCT/SE96/01508 filed Nov. 20, 1996, which was published as WO 97/19347.

The present invention relates to a chromatographic method for separating one or several organic substances in a liquid sample by passing said sample of substances through a chromatographic device and a chromatographic device for that separation. More precisely the invention relates to a separation method on a chromatographic device and the chromatographic device which contains as separating medium a continuous macroporous matrix. The separation medium is prepared by polymerization of a high internal phase emulsion system.

A common type of separation technique widely used in modern biotechnology is column chromatography. The chromatographic separation is carried out by forcing a liquid through a column packed with a matrix consisting of particulate beads. A sample which can be a mixture of e.g different proteins is introduced at the top of the column and then moves with the flow through the column. The proteins or substances will be retarded on the matrix in such a manner that proteins having different properties, e.g charge, size, hydrophobicity etc, will be retarded differently and therefore separated.

It is desirable that the separation should occur with fast kinetics and low band broadening in order to obtain a fast separation and to be able to well resolve the different substances from each other. To achieve this, the diffusive transport of the substances in and out of the beads has to be minimized, since this will cause band broadening and thus loss in resolution. The band broadening effects will increase with increasing flow rates and with increasing particle size. These effects have led the manufacturers of high performance chromatography media to reduce the size of the beads. However, small beads bring about other problems. Above all, packing with smaller beads gives a higher back pressure due to the narrowing of the convective flow channels in between the particles in a packed bed. To compensate for the increased back pressure a shorter column can be used which generally results in a lower separation capacity, or the column and fluid pumps can be redesigned to withstand higher pressure with accompanying costs. It is also difficult and expensive to prepare a perfectly packed column from particulate matrices.

To solve the problem with diffusive transport in and out of the beads it has been suggested to use a stationary phase shaped as a continuous porous plug. WO 90/07965 discloses a continous, coherent gel plug formed by bulk polymerization of monomers in such a way that the polymer chains adhere to each other in bundles with voids or channels formed between the bundles. In a later publication the inventor of this patent application states that this plug can not be used for chromatography, as the plug collapses when pressure is applied. Instead he recommend to compress the gel plug 10–15 fold. The compression would result in non-uniform channels in the plug and produce very high back pressures.

U.S. Pat. No. 5,334,310 relates to a continous macroporous polymer plug containing small pores having diameters less than about 200 nm and large pores with diameters greater than about 600 nm. The porous plug is produced by bulk polymerization of vinyl monomers in the presence of a porogen. A very high separation efficiency, easiness to prepare and versatility in the selection of monomer chemistry are advantages mentioned for the plug contained in a column. Due to the irregular structure of the pores in the plug and pores with rather small median size, also this plug results in separation at relatively high back pressures.

Therefore, there is a need for a further improved chromatographic separation method and a chromatographic device therefore.

Thus, the object of the present invention is to provide an improved chromatographic separating method and a chromatographic device with a separation medium without the disadvantages mentioned above.

A further object of the invention is to present a chromatographic separation method and a device comprising a medium with fast kinetics, with high efficiency, with good mechanical properties and with low back pressures.

It is yet another object of the invention to obtain a separating method and medium especially suitable for separating large biomolecules or aggregates.

The objects of the invention are achieved by the method of chromatographic separation and by the chromatographic device as claimed in the claims. According to the invention a chromatographic method for separating one or several organic substances in a liquid sample is obtained, in which said sample of substances is passed through a chromatographic device containing as separation medium at least one continuous macroporous matrix. The macroporous matrix comprises a cross-linked organic polymer prepared by polymerisation of a high internal phase emulsion system of a water-in-oil emulsion of organic monomers. The emulsion contains at least 75% by weight of water phase, and the polymerisation results in an open porous structure, to allow a convective flow to pass through the macroporous matrix, whereby said organic substances separate from each other and/or the liquid. The pores of the macroporous matrix can be unmodified, or surface modified in a manner,that the convective flow is not hampered.

Further according to the invention a chromatographic device is obtained which contains as separation medium at least one continuous macroporous matrix. The macroporous matrix comprises a cross-linked organic polymer prepared by polymerisation of a high internal phase emulsion system of a water-in-oil emulsion of organic monomers, said emulsion containing at least 75% by weight of water phase, said polymerisation results in an open porous structure, to allow a convective flow to pass through the macroporous matrix. The pores of the macroporous matrix can be unmodified, or surface modified in a manner,that the convective flow is not hampered.

It has been found that by preparing the macroporous matrix by polymerisation of the monomers in the form of a high internal phase emulsion, a method is obtained by which the organic substances separate from each other in the chromatographic device at low back pressures, with high theoretical plate numbers over a broad range of linear flow rates and that the mass transfer is driven by convective flow in the matrix pores.

The production of polymeric materials by polymerization of a water in oil emulsion having a high internal phase ratio of water to monomer have been known quite long. DE 1 160 616 and DE 1 494 024 disclose the production of porous polymers for isolation materials by polymerization of a high internal phase emulsion of water-in-oil type. The water content of the emulsion can be up to 98%.

EP 60 138 relates to cross-linked polymeric materials with low density and high absorbency. The material is produced by vinyl polymerization from a water-in-oil emulsion, where the emulsion contains at least 90% by weight of water. None of these patents relates to chromatography. EP 288 310 relates to a substrate comprising a porous cross-linked polymeric material filled with a gel material. The polymeric material is prepared by the high internal phase emulsion technique as described in EP 60 138. The substrate is used for peptide synthesis but chromatography is also mentioned as a possible field of use. However, the peptide synthesis is made on the gel, whereas the function of the cross-linked polymeric material is as a ridgid framework to enclose the gel. There is no disclosure or examples that the polymeric material could be used as stationary phase in chromatography. Less is there any information of the advantages of a plug of such a material as the stationary phase in column chromatography. On the contrary, the invention disclosed in EP 60 138 would not function in a method using the continuous matrix for chromatography, since the gel filled pores would not allow convective flow through the matrix. In EP 288 310 the substrate is used in particulate form. The material is crushed, and packed in the column. The drawbacks with a packed column, as mentioned in the introduction, are then also obtained.

The improvement with the method and the chromatographic device according to the invention is related to the macroporous cross-linked organic polymer. The polymer is prepared with the so called HIPE technique (High Internal Phase Emulsion). According to this technique a high amount of water is emulsified into the monomer phase, which is the oil phase. The water phase can optionally contain one or more dissolved salts, e.g. sodium chloride, sodium sulphate, ammonium sulphate etc. The emulsion contains at least 75% by weight of water based on the monomer/water composition. Preferably the emulsion contains at least 90% by weight of water phase. The polymerisation of the emulsion results in a material with a very open and regular three dimensional structure. In the polymer structure an open pore foamlike structure is built up by cavities in the form of spheres with connecting pores between the spheres so that a continuous void or pore phase is formed throughout the matrix. This structure has a low solid content, down to a few per cent, but very good mechanical qualities. The open structure of the matrix enables a convective flow with very low back pressure even at high flowrates.

In contrast to the matrix of the chromatographic device according to the invention, bulk polymerisation with a porogen as used e.g. in U.S. Pat. No. 334,310 for the production of the matrix, results in a more irregular structure, composed of clustered aggregates. In this manner there are often obtained two descrete classes of pores, the through flow pores and the separation pores. The through flow pores are the voids between the aggregates and the separation pores are the pores in the aggregates. This matrix has a lower mechanical strength, a higher matrix content, at least 30% of the matrix by volume, and a much higher back pressure, usually 10 to 50 times higher than a matrix prepared by the HIPE technique.

To obtain a high internal phase water-in-oil emulsion, the monomers in the oil phase must be hydrophobic. The cross-linked polymer of the matrix is normally prepared by free radical polymerization of hydrophobic monomers and crosslinkers. Suitable monomers include one or more alkene groups, i.e. a substituted or non-substituted vinyl group (monofunctional, difunctional and polyfunctional vinyl monomers). As preferred monomers can be mentioned derivatives of styrene monomers, vinyl benzene, hydrophobic acrylate or methacrylate monomers,such as dodecyl methacrylate, octadecyl methacrylate, perfluoroalkylacrylates, derivatives of acrylamides and monomers containing functional groups such as glycidyl methacrylate. As crosslinkers can be used any di or polyfunctional vinyl monomer e.g divinylbenzene, alkane diol acrylates or methacrylates e.g. ethylene glycol dimethacrylate, butan diol dimethacrylate, hexane diol dimethacrylate and trimethylol propane trimethacrylate.

The chromatographic qualities of the macroporous matrix are dependent on pore structure. A change in the pore size influences the surface area, the number of theoretical plates, the pressure-flow characteristics etc. The choice and amount of emulsifier are important for the pore structure. The emulsion shall always contain an emulsifier which will provide an inverse emulsion together with water and oil phase (see DE-A-1160616 and EP-A-60138). Suitable emulsifiers are monoesters of $C_{10-25}$ carboxylic acids and sugar alcohols and block copolymers containing both hydrophilic and hydrophobic segments, for example sorbitane monooleate and polyethyleneglycol polyhydroxystearic acid.

The amount of emulsifier for stable emulsions lies normally within the range 0.5–30% by weight in relation to the oil phase.

Another important parameter influencing the pore size is the content of water of the emulsion. If the content increases from about 90% to 95% the pore size will increase resulting in a more open structure of the matrix.

Generally the diameter of the pores cf the matrix lies between about 0.5–100 μm. Preferably the macroporous matrix contains spherical pores with a pore diameter between 3–25 μm, most preferably 5–25 μm and connecting pores with a pore diameter between 0.5–15 μm.

The emulsions are prepared by mixing the monomers, the emulsifier/s and the initiator if an oil-soluble one is used. Otherwise the water-soluble initiator is dissolved in the water. When the oil phase is homogeneous, water is added slowly. The mixture is vigorously stirred. The emulsion is added to a mold and the temperature is preferably raised to start the polymerisation. The emulsion can be prepared at ambient temperature. The polymerization temperature can be varied during the polymerization process but it is important that the temperature is controlled so that the emulsion will not collaps. Generally the temperature should be kept at least 10° C. below the boiling point of water and the boiling point of the other components, normally below 90° C. Suitably the emulsion can be kept initially at one temperature for polymerization whereafter the temperature is raised to further cure the product.

The polymerization can be initiated by conventional radical initiators. The initiators may be either water-soluble or oil-soluble. Examples of initiators are azo-compounds (oil-soluble), hydrophobic peroxides (oil-soluble),perbenzoates (oil soluble), persulphates (water-soluble), different redox systems, e.g hydrogen peroxide+water (Fenton's reagent, water soluble) or aniline+benzoyl peroxide (oil soluble).

Polymerization may also be initiated via UV radiation, γ-radiation, electron beam radiation etc. After polymerisation the polymer matrix is washed and used in a chromatographic separation device. The separation device can be in a wide variety of shapes and formats. The device can either be in the form of a holder containing the matrix, or the device can be a self-supporting form of the matrix. As example of holders can be mentioned columns, filled pipette tips, syringes, spiral form, tubes etc. Self-supporting device can for example be in the form of slabs, microtiter plates and hollow cylinders. A preferred embodiment of the device is a column containing one or several matrices.

The liquid may be forced through the matrix by pumping, suction, centrifugal forces or gravity.

The matrix may be shaped into the desired configuration directly in the mould, or it can be shaped after the polymerization by cutting, drilling, sawing etc. into the desired shape e.g a plug, cylinder, brick, sheet, tablet, plate or slab.

The separation device contains at least one matrix entity but it is possible to use two or more matrices in the same device to increase the length of the separation medium, or to stack matrices with different functionalities on top of each other. The size of the matrices will depend on the dimensions of the device and can vary from short capillaries to very large columns with up to 1 m in diameter and 2 meters in bed height.

A suitable configuration of the matrix is a cylinder which is inserted into an empty column. The matrix should have a diameter slightly larger than the diameter of the column to be used. The matrix is pressed into the column to ensure that it seals against the column wall. Thereby the flow is forced through the whole area of the matrix. This manner of matrix production is preferable for all types of cylindrical columns except for capillary columns. It is generally not suitable to cast the matrix directly in the column as described in U.S. Pat. No. 5,334,310, as the polymer matrix shrinks during the washing procedure. This can lead to leakage between the matrix and the column wall.

The column as such, according to the invention, can be any conventional column, with material, shape and size being varied within wide limits. The column tube should be substantially rigid and can be made of, for example, metal such as stainless steal or titan, glass or a rigid polymer. The adaptors and spreader of ordinary columns, designed for traditional particulate media, are however, usually less suitable to use according to the invention, as they require a back pressure from the matrix in order to distribute the sample over the whole matrix area. The matrices according to the invention are highly porous and create almost no back pressure. As the radial diffusion of the sample in the matrix is very limited, the sample has to be thoroughly spread out before it penetrates the end surface of the matrix. Otherwise the flow will only pass a smaller part of the volume of the matrix. An adaptor with a centered inlet and a spreader cone, in the top of the column, which will distribute the sample over the whole matrix is preferred. In the bottom the adaptor can be a so called ring spreader, optionally with a supporting net. A suitable arrangement of adaptors is disclosed in PCT/SE95/00632.

For very narrow columns, i.e. capillary columns, it is possible to directly cast the plug in the column. With capillary columns is meant columns with a diameter less than about 2 mm and lengths between about 10–10000 cm. Capillary columns can be made from capillary material that adheres to the polymerized material even after washing. This will inhibit the formation of a gap between the matrix and the capillary wall and ensures that the flow passes through the whole cross-section of the capillary. Thus it has been found that capillaries made out of steel gives good adhesion and the matrix can be cast directly in such a capillary and separate organic molecules, while in a capillary made out of titanum, a gap will form between matrix and wall, thus impairing the separation.

Columns can also be made in a mould consisting of e.g. teflon® tubing, and in a second step transfer the free standing capillary to shrinkage tubing and/or cast a polymer resin around the capillary to ensure that no flow passes between matrix and column wall.

According to the method of invention, separation can be done at a very low back pressure and with high theoretical plate numbers. With a low back pressure is meant 0.02–2 bar/cm column length at a linear velocity of 1000 cm/hour. High theoretical plate numbers means about 2000 100.000 theoretical plates/m.

A further embodiment of the invention is separation on a column containing a matrix having a secondary pore structure within the matrix walls. This structure is produced by adding a solvent to the oil phase of the water-in-oil emulsion. The extent and size of the created secondary pore structure is controlled by the choice of solvent. By this method the surface area can be increased e.g. from 10 $m^2$ /g to up to about 500 $m^2$/g. The chromatographic performance is for some applications, e.g reversed phase separation of peptides, improved by introducing a secondary pore structure, whereas the mechanical stability of the material is decreased. Two different types of solvent can be used. One is a solvent for the formed polymer and works by swelling the formed polymeric network. The obtained pores are very small usually less than 500 Å. The other type is a solvent for the monomer but precipitates the polymer, a so called porogen. There is a phase separation between the porogen and the polymer during polymerisation. The resultant pores are usually within the size 500 Å–10000 Å. The choice of solvent for the production of matrix according to the invention is different compared with porous particles according to the suspension procedure. In the latter case it is common to use some higher alcohol or carboxylic acid. However, these porogens have surface active qualities which leads to destabilisation of the emulsion. Suitable porogens for the high internal phase emulsion are alifatic and aromatic hydrocarbons, e.g. n-hexane, n-octane, ri-dodecane and toluene.

According to a further aspect of the method according to the invention the pores of the porous matrix are surface modified in a thin layer in such a way that the pores are not clogged or filled, to allow a convective flow to pass through the porous matrix. Preferably the thin layer is less than 2 $\mu$m, most preferably between 0.0005–0.5 $\mu$m. Suitably the pores are surface modified with with ion exchange ligands, hydrophobic ligands, chelating ligands or affinity ligands or by physical adsorption or covalent coupling of a hydrophilic polymer which can be cross-linked. The hydrophilic polymer can then be derivatized with ion exchange ligands, hydrophobic ligands, chelating ligands or affinity ligands. As suitable hydrophilic polymers can be mentioned phenyldextrane, allyldextrane, agarose and derivatives thereof, water soluble cellulose derivatives, starch derivatives and water soluble synthetic polymers such as polyvinylalcohol and derivatives thereof, poly (hydroxyethyl vinyl ether) and derivatives thereof, polyethyleneglycol, poly (hydroxy ethyl acrylates), polyacrylic acids, poly(vinyl N-pyrrolidone) and polyacrylamides among many others.

The method and device according to the invention can be used for separation of all types of organic molecules, but preferably for separation of biomolecules, especially large biomolecules or aggregates with a molecular weight over 100.000 Daltons, since the large pores of the matrix will not exclude even very large molecules, with up to 10.000.000 Daltons in molecular weight. Example of such molecules are proteins, peptides, nucleic acids, oligonucleotides, cells or viruses. The macroporous matrix used according to the invention has a highly hydrophobic surface and thus is very suitable for reversed phase chromatography. However, as mentioned above the surface can be modified and the macroporous matrix can then be used in other common liquid chromatography methods such as ion exchange chromatography, hydrophobic interaction chromatography or affinity chromatography.

BRIEF DESCRIPTION OF THE DRAWINGS

The invention will now be illustrated with the following examples, which however are not intended to limit the invention. The results from the examples are shown in the figures, whereby FIG. 1 relates to an RPC separation of five peptides in example 5.

DESCRIPTION OF THE PREFERRED EMBODIMENTS

Figure 1:
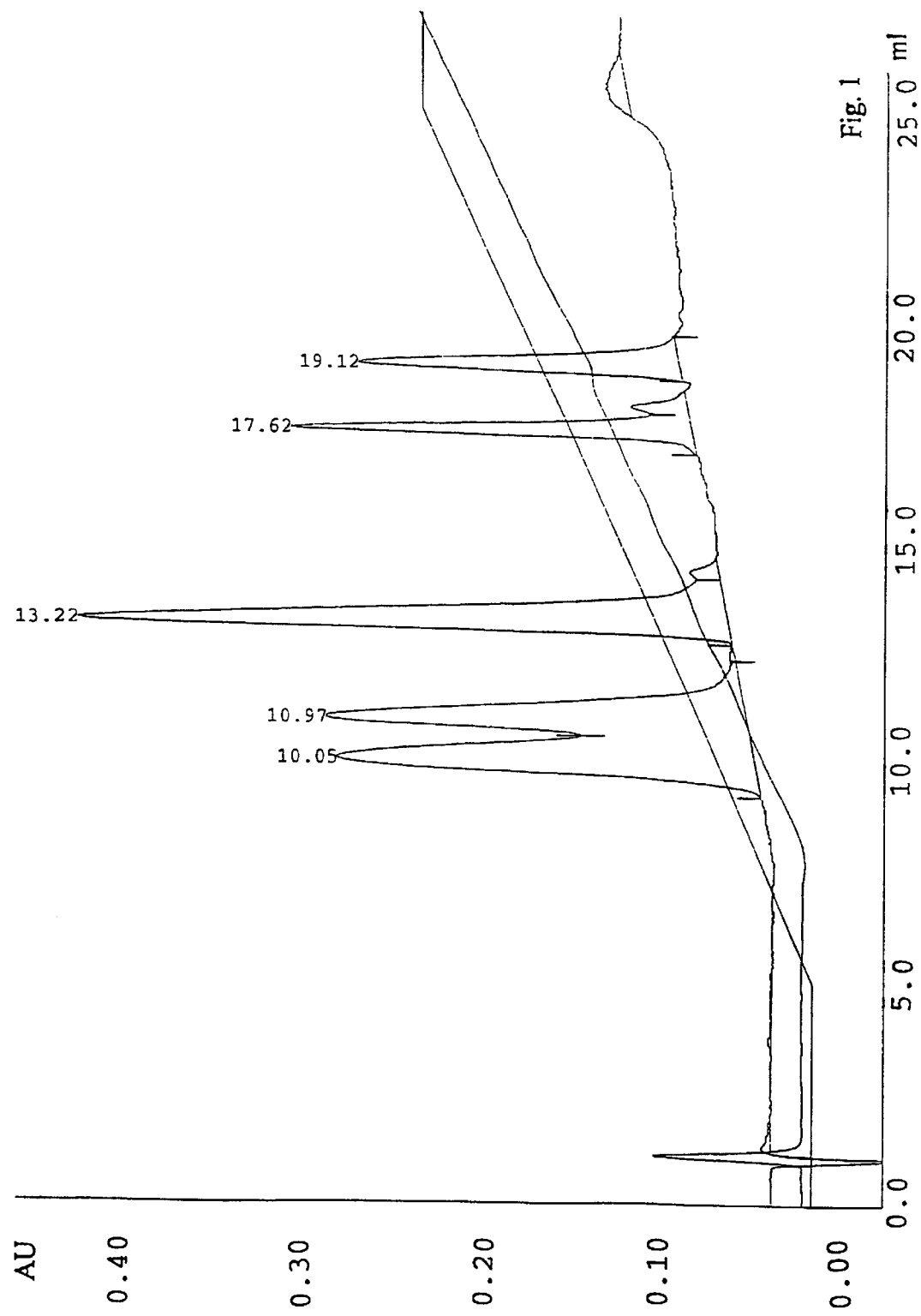

Flow Properties and Plate Numbers of the Continuous Matrices.

The matrix was then cut out to two different dimensions, with about 0.05% larger matrix diameter than the column diameter:

a) 16 mm in diameter and 50 mm in length (16/50)

b) 35 mm in diameter and 10 mm in length (35/10)

The shaped matrices were pushed into columns with 16 mm and 35 mm respectively in diameter. As shown in PCT application SE95/00632 the mounting and design of flow distribution is of high importance to achieve high plate numbers.

Matrices with different pore size and solids content were made by varying monomer content and emulsifier composition. Size of cavities and connecting pores was estimated from scanning electron microscopy.

Using the formula $N=16(t_r/w)^2/L$ where N is the number of plates, $t_r$ is elution volume in ml, w is peak breadth at baseline in ml, and L is the length of the column, plate numbers were calculated from a pulse of 50 microliter $NaNO_3$ in 0.5 M NaCl using 0.5 M NaCl as buffer in a Pharmacia FPLC™ liquid chromatography system equipped with a UV monitor.

The matrices in general showed very good flow properties together with high plate numbers. The results are shown in table 1.

| Ex. no | Hypermer (g) | SPAN 80 (g) | water (g) | cav. size (µm) | pore size (µm) | cm/h at 3 bars for | | plate hight in µm at flow rate in cm/h | | |
|---|---|---|---|---|---|---|---|---|---|---|
| | | | | | | 16/50 | 35/10 | 300 | 1000 | 300 |
| 1 | 0.7 | 2.2 | 260 | 10–20 | 1–8 | 2000 | 4000 | 29 | 32 | 23 |
| 2 | 0.7 | 2.2 | 555 | 15–25 | 3–15 | 7000 | 5000 | 33 | 32 | 30 |
| 3 | — | 5.2 | 281 | 3–8 | 0.5–3 | 200 | 1000 | 34 | — | 24 |
| 4 | — | 5.2 | 414 | 3–8 | 0.5–3.5 | 300 | 1000 | 57 | — | 19 |

EXAMPLE 1–4

Synthesis of Matrices 0.3 g of the initiator 2,2-azobis(2,4-dimethylvaleronitrile) was dissolved in the oil phase consisting of 13 g styrene and 13 g divinylbenzene together with the surfactants which were Hypermer® B261 (ICI) and sorbitanmonooleate (SPAN®80 from Fluka). The oil phase was transferred to a 500 ml reactor equipped with a stirrer. The stirring speed was set to 500 rpm and water was slowly added, 2–4 ml per minute. When all water had been added the stirring continued for another 15 minutes.

The highly viscous water-in-oil emulsion was then transferred to a teflon coated 225 ml mould which was heated at 50° C. for 16 hours and then at 70° C. for another 24 hours. The polymerized continuous matrix was taken out of the mould and transferred to a column with rubber tubing along the wall. By applying pressurized air the tubing was inflated and was pressed against the continuous matrix. The matrix was first washed with 3 column volumes of acetone, then with a gradient going from acetone to water over 10 column volumes and finally with 3 column volumes of water. During washing the matrix will shrink, but the inflated tubing ensures that the matrix has a tight fitting to the column during the wash steps.

Flow measurements on empty columns gave a linear flow at 3 bars of 20.000 cm/h for the 16/50 column and 5000 cm/h for the 35/10 column.

Peptide Separation Using a Reversed Phase Continuous Matrix.

EXAMPLE 5

A water-in-oil emulsion was made as in example 1. Slightly conical HDPE (high density polyethylene) columns in diameter was filled with the highly viscous emulsion and was then heated overnight at 50° C. and at 70° C. for another 24 hours. The columns were thoroughly washed with acetone and water.

Cylinders 5.5 mm in diameter and 10–15 mm in height were cut out from the matrix and pushed into an HR 5/5 column (Pharmacia Biotech). Several cylinders were placed on top of each other in the same column giving a total length of 5 cm. The column was mounted in a FPLC™ liquid chromatography system with 0.125% trifluoractic acid (aq) in buffer A and a 90/10 mixture of acetonitrile water containing 0.1% trifluoracetic acid in buffer B.

25 µl of a sample mixture containing 12.5 µg of five peptides (val5Angiotensin II, Angiotensin III, Angiotensin I, Insulin B chain, all from Sigma, and HGRF 1-29 from Pharmacia Biotech) was loaded onto the column. The sample was eluted with a gradient going from 5% B buffer to 45% B buffer over 20 column volumes. Flow rate was 1 ml/min. The mixture was separated into 5 peaks, the last three with baseline resolution, the two first were not fully separated from each other. See FIG. 1.

EXAMPLE 6

Figure 2:
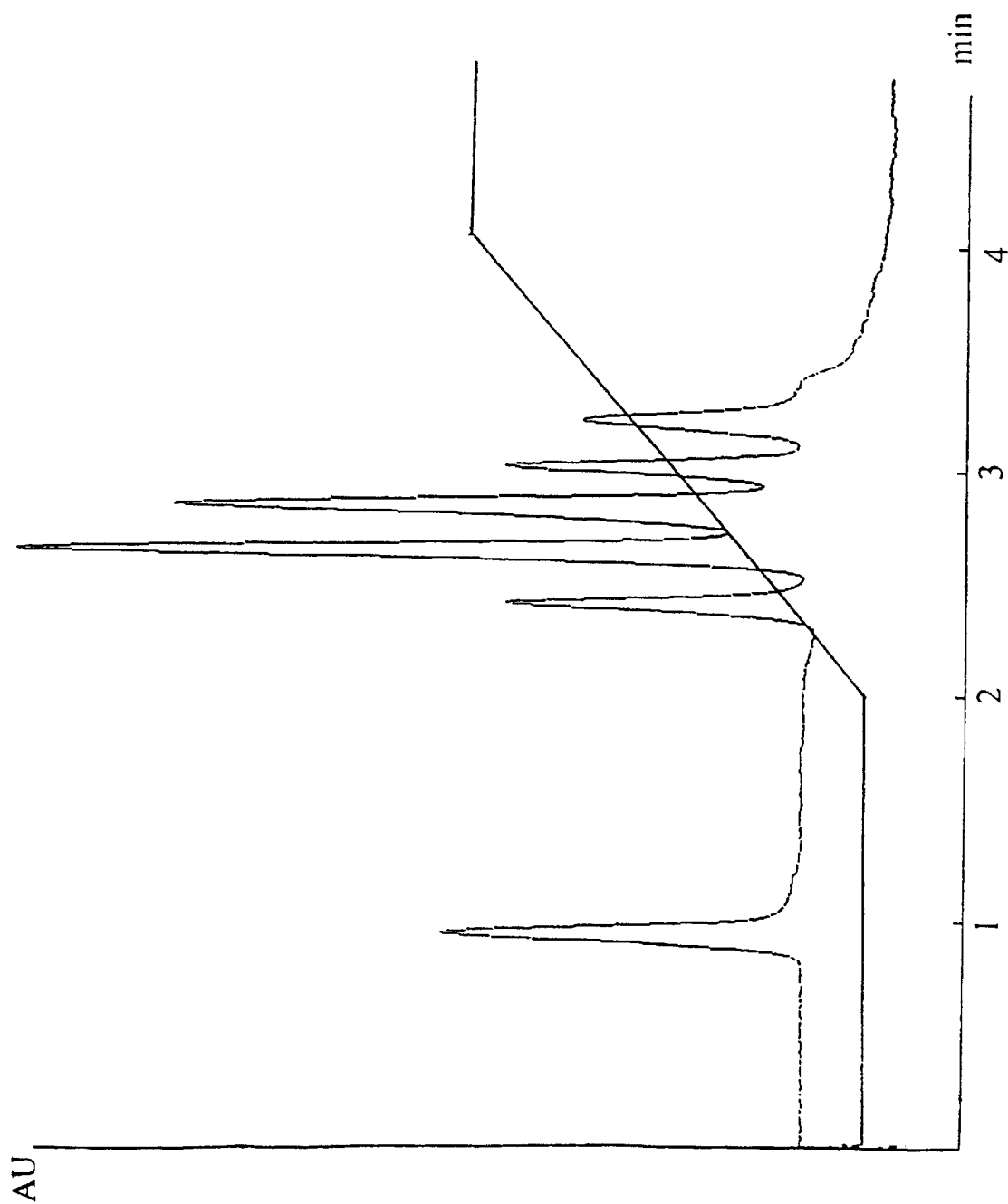
FIG. 2 relates to an RPC separation of five proteins in example 6.

A continuous 16/50 column was prepared as in example 1 and mounted in a Pharmacia LKB HPLC system. 100 µl of a mixture containing 0.5 mg of five proteins (Ribonuclease A, Cytochrome C, Lysozyme, Albumin and b-lactoglublin, all from Sigma) were loaded on the column and eluted with gradient going from 18% acetonitrile to 54 acetonitrile in 2 column volumes. Flow rate 10 ml/min. The proteins eluted in five well separated peaks in less than two minutes. See FIG. 2.

Protein Separation Using a Ion Exchange Continuous Matrix.

EXAMPLE 7

A 16/50 column containing a continuous matrix was prepared as in example 1. An aqueous solution containing 2% (by weight) of phenyldextrane (mol. weight 500.000, substitution degree 0.2 phenyl groups per monosaccharide) was pumped through the column with 4 ml per minute for 16 hours. The column was washed with four column volumes of water.

Through a T-connection, 2 ml/min of 2 M sodium hydroxide and 2 ml/min of 35% glycidyltrimethylammoniumchloride were mixed and pumped through the column for 4 hours. The column was then washed with 10 column volumes of pure water and 5 column volumes of 1 M sodium chloride.

The obtained ion exchange column had an ion capacity of 5.6 µmole Cl$^-$/ml matrix.

Dynamic capacity was measured by running a breakthrough curve with BSA using an FPLC™ liquid chromatography system and 1 mg BSA/ml in a buffer solution containing 50 mM tris(hydroxymethyl)-aminomethane (pH 8). The dynamic capacity was found to be independent of flow rate, 5 mg BSA/ml for both 300 and 1000 cm/h.

Figure 3:
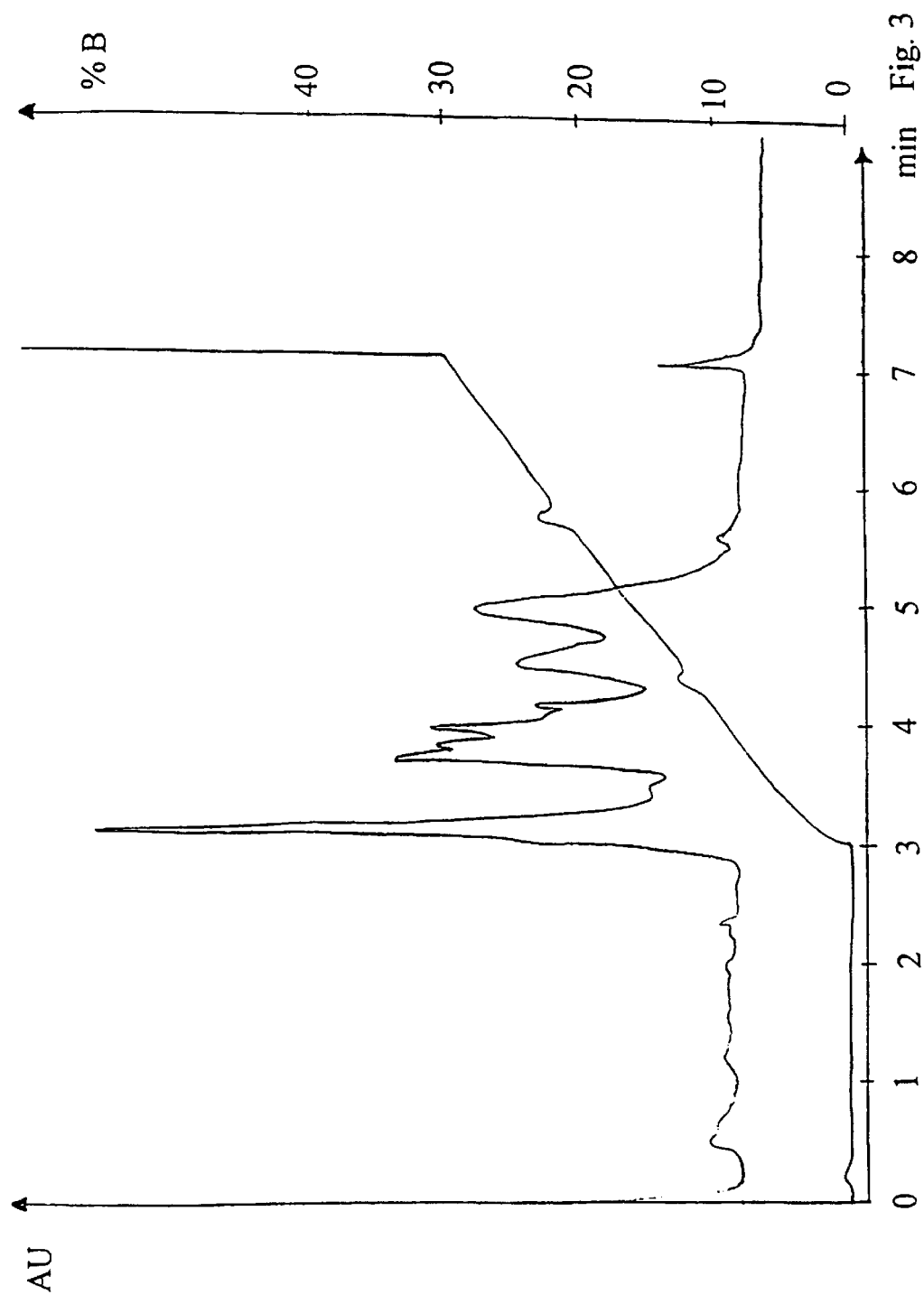
FIG. 3 relates to an ion exchange chromatography separation of four proteins in example 7.

A separation was performed with a mixture containing 0.5 mg transferrin, 1.0 mg ovalbumin and 1.0 mg b lactoglobulin (A and B) in 10 mM piperazine, pH 6, by gradient elution going from 0–0.3 M sodiumchloride over 9 column volumes. The proteins separated with good resolution (FIG. 3), and the resolution was retained over a broad range of flow rates, 300–1500 cm/h.

Acrylate Matrix as an Continuous RPC Media.

EXAMPLE 8

0.15 g V-65® (azobis(dimethylvaleronitrile), 1.1 g SPAN® 80, 035 g Hypermer® B261 were dissolved in 6.5 g octadecylmethacrylate and 6.5 g ethyleneglycoldimethacrylate in a 250 ml beaker. 130 g water were added dropwise with stirring over 10 minutes. Slightly conical HDPE columns 1 cm in diameter were filled with the high viscous internal emulsion and was then heated overnight at 50° C. and at 70° C. for another 24 hours. The columns were thoroughly washed with acetone and water, and then plugs with 5 mm in diameter were cut out of the filled HDPE columns. The plugs were pushed into a HR 5/5 column, and the same peptide separation as in example 5 was performed giving roughly the same resolution and selectivities.

Perfluorinated Matrix as Continuous RPC Media

EXAMPLE 9

A solution was prepared of 4.8 g hlexadekafluorodecyl methacrylate, 8.2 g technical divinylbenzene (60%), 0.15 g V-65, 1.1 g sorbitan monooleate and 0.35 g nonionic polymeric surfactant (Hypermer B261). 130 g water was added during 10 min and emulsified in the organic phase with a Collomixer stirrer propeller at 400 rpm. The viscous emulsion was poured into a HDPE container and left to polymerize at 50° C. for 24 h. A solid plug was formed, which was trimmed at the upper and lower ends. The porous plug was then washed by acetone and water consecutively pumped through the material, and then plugs with 5 mm in diameter were cut out of the filled HDPE columns. The plugs was pushed into a HR 5/5 column, and the same peptide separation test as in example 5 was performed giving roughly the same resolution and selectivities.

Continuous matrices with large surface area as RPC media.

EXAMPLE 10–11

0.19 g SPAN 80, 0.06 g Hypermer B261, 2.24 g divinylbenzene (65%), 2.24 g styrene, 0.05 g azobisdimethylvaleronitrile and organic solvent were mixed in a 250 ml beaker, and 46 g water was added dropwise while stirring with a magnetic stirrer. Slightly conical HDPE columns 1 cm in diameter were filled with the high viscous water-in-oil emulsion and heated overnight at 50° C., then at 70° C. for another 24 hours. The columns were thoroughly washed with acetone and water, and then plugs with 5.5 mm in diameter was cut out of the column.

Surface area measurements were made with nitrogen adsorption (BET method) which showed that the addition of organic solvent increased the surface area.

| Example | solvent | amount (g) | surface area m$^2$ |
|---------|---------|------------|--------------------|
| 5 | none | — | 10 |
| 10 | octane | 1.26 | 46 |
| 11 | toluen | 2.24 | 66 |

Figure 4:
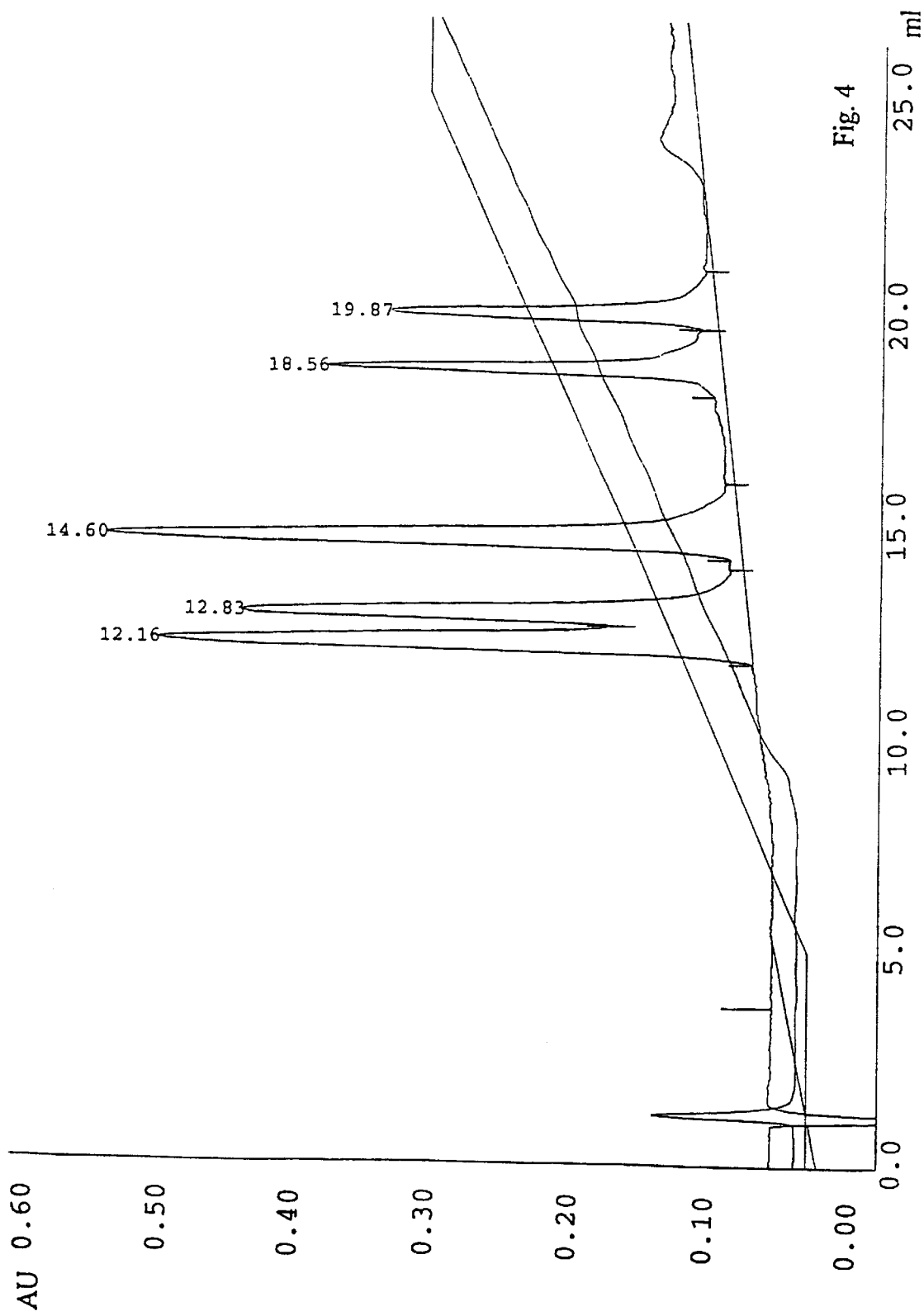
FIG. 4 relates to an RPC separation of five peptides in example 10. In the figures AU means absorbance.

The plugs were pushed into a HR 5/5 column as in example 5, and the same peptide separation was performed, giving an improved resolution with both example 10 and 11 compared with the low surface area matrice in example 5. See FIG. 4.

Continuous Matrix in Shrinking Tubing.

EXAMPLE 12

An inverse emulsion was prepared according to the procedure in example 1. With a syringe, a glass column, 5 mm in diameter and 115 mm in length was filled with the emulsion. The tubing was heated at 50° C. over night and then at 70° C. for another 3 hours. The tubing was washed with acetone and water, which caused the continuous matrice tube to shrink to 4.85 mm in diameter. The matrice was taken out of the teflon coating and was then placed in a shrinkage tubing FIT-221 (crosslinked polyolefin from ELFA) which was heated to 1200 so that it shrank to a tight fitting around the matrice tube. The shrinkage tubing with matrice was then placed in another shrinkage tube which was sealed at one end and then filled with epoxy mould (Permabond® E27 from Sikema) which was cured at 50° C. for 1 hour.

The cured epoxy mould was strong enough to permit flows up to 1 ml/min without getting leakage between the matrice and the inner wall of the tubing. A separation was performed with a peptide mixture as in example 5, with similar results regarding resolution and selectivity.

Continuous Matrix in Long Capillaries.

EXAMPLE 13

An inverse emulsion was prepared according to the procedure in example 1. With a syringe, a 2100 mm long steel capillary (0.75 mm inner diameter) was filled with the emulsion which was polymerized by heating at 50° C. overnight and than at 70° C. for another three hours.

The steel capillary containing continuous matrix was then washed with acetonitrile containing 0.1% trifluoracetic acid. When casted in this capillary, the matrix could be washed without shrinkage. Shrinkage of the matrix will form a gap which would cause the flow to pass between the matrix and the inner wall of the capillary, thus disrupting any separation.

In a SMART™ liquid chromatography system (Pharmacia Biotech) the same peptides as in example 5 were separated by gradient elution with acetonitrile, with a slightly lower resolution than achieved in example 5. Even though the column was very long and narrow, the back pressure was still kept at a relatively low level, 30 bars at a flow rate of 1400 cm/h.

What is claimed is:

1. A chromatographic method for separating one or several organic substances in a liquid sample characterized in passing said sample of substances through a chromatographic device containing as separation medium at least one continuous macroporous matrix, said macroporous matrix comprises a cross-linked organic polymer prepared by polymerisation of a high internal phase emulsion system of a water-in-oil emulsion of organic monomers, said emulsion containing at least 75% by weight of water phase, said polymerisation results in an open porous structure, to allow a convective flow to pass through the macroporous matrix, whereby said organic substances separate from each other and/or the liquid and the pores of the macroporous matrix are unmodified, or surface modified in a manner that the convective flow is not hampered.

2. A method according to claim 1, characterized in that the organic substances separate from each other in the chromatographic device at a low back pressure, with high theoretical plate numbers over a broad range of linear flow rates and that the mass transfer is driven by convective flow in the matrix pores.

3. A method according to claim 1, characterized in that said emulsion contains at least 90% by weight of water phase.

4. A method according to claim 1, characterized in that the chromatographic device contains two or more matrices.

5. A method according to claim 1, characterized in that the cross-linked organic polymer is prepared by free radical polymerisation of hydrophobic monomers and cross linkers.

6. A method according to claim 5, characterized in that the monomers are styrene/divinylbenzene.

7. A method according to claim 5, characterized in that the monomers are hydrophobic acrylate or methacrylate monomers cross-linked by alkane diol acrylates.

8. A method according to claim 1, characterized in that the diameter of the pores of the macroporous matrix lies between about 0.5–100 $\mu$m.

9. A method according to claim 8, characterized in that the macroporous matrix contains spherical pores with a pore diameter between 3–25 $\mu$m and connecting pores with a pore diameter between 0.5–15 $\mu$m.

10. A method according to claim 1, characterized in that the oil phase of the water in oil emulsion contains a solvent.

11. A method according to claim 1 characterized in that the pores of the porous matrix are surface modified in a thin layer in such a way that the pores are not clogged or filled, to allow a convective flow to pass through the porous matrix.

12. A method according to claim 11, characterized in that the thin layer is less than 2 $\mu$m.

13. A method according to claim 11, characterized in that the pores are surface modified with ion exchange ligands, hydrophobic ligands, chelating ligands or affinity ligands.

14. A method according to claim 11, characterized in that pores are surface modified by physical adsorption or covalent coupling of a hydrophilic polymer which can be cross-linked.

15. A method according to claim 14, characterized in that the hydrophilic polymer is derivatized with ion exchange ligands, hydrophobic ligands, chelating ligands or affinity ligands.

16. A method according to claim 1, characterized in that the organic substances separate by reversed phase chromatography, by ion exchange chromatography, by hydrophobic interaction chromatography or affinity chromatography.

17. A method according to claim 1, characterized in that the organic substances are biomolecules.

18. A method according to claim 17, characterized in that the biomolecules are selected from the group consisting of proteins, peptides, nucleic acids, oligonucleotides, cells or viruses.

19. A method according to claim 1, characterized in that the device is a column.

\* \* \* \* \*